United States Patent [19]
Nakagawa et al.

[11] 4,393,257
[45] Jul. 12, 1983

[54] PROCESS FOR PREPARING BENZOTRIFLUORIDE AND ITS DERIVATIVES

[75] Inventors: Tsuneo Nakagawa; Uji Hiramatsu; Toshihide Honda, all of Osaka, Japan

[73] Assignee: Daikin Kogyo Co., Ltd., Osaka, Japan

[21] Appl. No.: 50,211

[22] Filed: Jun. 20, 1979

Related U.S. Application Data

[63] Continuation-in-part of Ser. No. 859,755, Dec. 12, 1977.

[30] Foreign Application Priority Data

Dec. 27, 1976 [JP] Japan .................................. 51-159033
Dec. 15, 1977 [IT] Italy .................................. 30726 A/77
Dec. 16, 1977 [DE] Fed. Rep. of Germany ....... 2756235
Dec. 27, 1977 [FR] France .................................. 77 39362

[51] Int. Cl.³ ............................................ C07C 17/20
[52] U.S. Cl. ............................. 570/145; 260/465 G; 568/936

[58] Field of Search ....................... 260/651 F, 465 G; 570/145; 568/936

[56] References Cited

U.S. PATENT DOCUMENTS 2,062,743 12/1936 Daudt et al. ..................... 260/651 F
2,121,330 0/1938 Scherer et al. .................. 260/651 F
3,755,477 8/1973 Firth et al. ....................... 260/651 F
3,966,832 6/1976 Lademann et al. .............. 260/651 F
4,012,453 3/1977 Nychka et al. .................. 260/651 F
4,080,392 3/1978 Ryf .................................. 260/651 F
4,155,940 5/1979 Marhold et al. ................. 260/651 F Primary Examiner—Charles F. Warren
Assistant Examiner—Joseph A. Boska
Attorney, Agent, or Firm—Birch, Stewart, Kolasch & Birch

[57] ABSTRACT

A process for preparing benzotrifluoride or derivatives thereof by contacting benzotrichloride or the corresponding derivatives with hydrogen fluoride in a gaseous phase in the absence of any catalyst, the contact being carried out in the presence of chlorine at an elevated temperature so as to accelerate the reaction rate.

6 Claims, No Drawings

PROCESS FOR PREPARING BENZOTRIFLUORIDE AND ITS DERIVATIVES

This is a continuation-in-part application of our co-pending application Ser. No. 859,755 filed Dec. 12, 1977.

The present invention relates to a process for preparing benzotrifluoride and its derivatives. More particularly, it relates to an improved process for preparing benzotrifluoride or a derivative thereof by reaction of benzotrichloride or the derivative corresponding thereto with hydrogen fluoride in the gaseous phase.

For preparation of benzotrifluoride from benzotrichloride and hydrogen fluoride, there have been known various procedures, none of which is satisfactory from the industrial viewpoint. For instance, the procedure for reacting benzotrichloride with hydrogen fluoride in the liquid phase at a temperature higher than 80° C. (cf. U.S. Pat. No. 1,964,244; Japanese Patent Publication (unexamined) No. 77324/1975) results in the formation of hydrogen chloride as a by-product during the reaction, whereby the pressure is much elevated. Accordingly, care must be taken concerning the stability in operation and the safety in working. In addition, an expensive high pressure reaction apparatus is needed. In order to avoid the above drawbacks, a procedure for carrying out the reaction by introducing benzotrichloride gradually into hydrogen fluoride in the liquid phase at a temperature lower than 19° C. under atmospheric pressure (cf. U.S. Pat. No. 3,136,822) has been proposed. However, this procedure has the disadvantage that a considerably long period of time for completion of the reaction is required. Besides, there are known numerous other procedures wherein the reaction of benzotrichloride with hydrogen fluoride is carried out in the presence of various catalysts (cf. U.S. Pat. No. 3,950,445). However, these procedures are disadvantageous in necessitating such catalysts for the reaction, showing only a lower conversion in the reaction under atmospheric pressure and requiring a long period of time for completion of the reaction.

Because of various drawbacks and disadvantages as seen in the procedures for carrying out the reaction of benzotrichloride with hydrogen fluoride in the liquid phase, attempts have been made to effect such a reaction in the gaseous phase in the absence of any catalyst. In this procedure, however, the reaction rate is extremely low so that benzotrifluoride can not be efficiently produced even at an elevated temperature.

As the result of an extensive study, it has now been found that the reaction of benzotrichloride with hydrogen fluoride in the gaseous phase in the absence of any catalyst can be remarkably accelerated in the presence of chlorine. It is notable that the remarkable enhancement of the reaction rate is produced under substantially atmospheric pressure. The present invention is based on the above finding.

According to the present invention, there is provided a process for preparing benzotrifluoride or a derivative thereof which comprises contacting benzotrichloride or a derivative corresponding thereto with hydrogen fluoride in the presence of chlorine in the gaseous phase at an elevated temperature.

In the process of this invention, the starting material is benzotrichloride or a derivative thereof (hereinafter referred to as "benzotrichloride compound"). As the derivative of benzotrichloride, there may be used any compound having a chemical structure constituted with a benzene ring and at least one trichloromethyl group thereon. In addition to at least one trifluoromethyl group, one or more substituents which do not materially interfere with the reaction between the trichloromethyl group and hydrogen fluoride may be optionally present on the benzene ring. Examples of such substituents are nitro, cyano, halogen (e.g. chlorine, bromine, iodine), etc. Thus, the term "benzotrichloride compound" includes those of the formula:

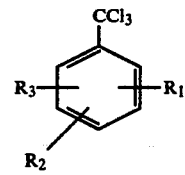

wherein $R_1$, $R_2$ and $R_3$ are each hydrogen, trichloromethyl, nitro, cyano or halogen, provided that one of $R_1$, $R_2$ and $R_3$ is nitro, each of the other two not being nitro.

The molar ratio of hydrogen fluoride to be used to the benzotrichloride compound may be usually from about 3 to 15, preferably from about 3.3 to 12. The molar ratio of chlorine to the benzotrichloride compound is normally not more than about 0.3, preferably from about 0.02 to 0.2. The use of chlorine in a higher amount than the said upper limit does not produce any advantage and may be rather unfavorable in producing a loss of the space or capacity.

In carrying out the process of the present invention, designed amounts of the benzotrichloride compound, of hydrogen fluoride and of chlorine (which is usually dissolved in the benzotrichloride compound to make a solution) may be charged, for instance, in a pre-heating apparatus and heated to make a gaseous mixture. The gaseous mixture is introduced into a reactor having a tubular shape, whereby the reaction proceeds at an elevated temperature. The reaction mixture exhausted from the reactor is introduced into a distillation tower, and gaseous materials such as hydrogen chloride, hydrogen fluoride and chlorine are taken out from the top of the tower while liquid materials including the produced benzotrifluoride or its derivative are obtained from the bottom of the tower.

The reactor may be made of any material resistant to corrosion by hydrogen fluoride, hydrogen chloride, chlorine and the like at an elevated temperature. Examples of such materials are stainless steel, nickel, nickel alloys (e.g. Inconel, Hastelloy), etc.

The elevated temperature in the reactor is varied with the kind of the benzotrichloride compound and may be usually from about 250° to 600° C., preferably from about 300° to 500° C. The contact time in the reactor is not limitative but is usually at least about 0.2 second, preferably not more than about 10 seconds. A higher temperature or a longer contact time over the said upper limits will unfavorably result in the increased production of tars or by-products. The pressure in the reactor is usually atmospheric but may be reduced or elevated.

The thus obtained liquid materials comprise benzotrifluoride or its derivative (hereinafter referred to as "benzotrifluoride compound"), which corresponds to the starting benzotrichloride compound. The derivative of benzotrifluoride may be the one having a chemical structure constituted with a benzene ring and at least one trifluoromethyl group thereon. In addition to at least one trifluoromethyl group, one or more substituents such as nitro, cyano, halogen and the like may be present on the benzene ring. Thus, the term "benzotrifluoride compound" includes those of the formula:

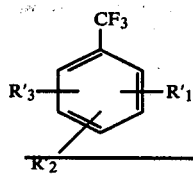

wherein $R_1'$, $R_2'$ and $R_3'$ are each hydrogen, trifluoromethyl, nitro, cyano or halogen, provided that one of $R_1'$, $R_2'$ and $R_3'$ is nitro, each of the other two not being nitro.

Recovery of the benzotrifluoride compound from the liquid materials may be carried out by a per se conventional separation procedure such as distillation.

The process of this invention is industrially advantageous in producing benzotrifluoride or derivatives thereof efficiently in high yields without using any expensive reacton apparatus even under atmospheric pressure.

Practical and presently preferred embodiments of the invention are illustratively shown in the following Examples wherein % and part(s) are by weight unless otherwise indicated.

EXAMPLES 1–6 AND COMPARATIVE EXAMPLES 1–2

Designed amounts of p-chlorobenzotrichloride (hereinafter referred to as "p-ClBTC"), m-nitrobenzotrichloride (hereinafter referred to as "m-NO₂BTC" or benzotrichloride (hereinafter referred to as "BTC") containing chlorine previously dissolved therein and of hydrogen fluoride are charged in a pre-heating apparatus, and the contents are heated to about 280° C. The resulting gaseous mixture is introduced into a "Hastelloy C" made tubular reactor (inner volume, 150 ml) with regulation of the feed amount, and the reaction is effected under the conditions as shown in Table 1. The reaction product coming out of the reactor is transferred to a distillation tower and distilled there.

From the top of the distillation tower, low boiling impurities such as hydrogen chloride, hydrogen fluoride and chlorine are exhausted, and from the bottom of the tower, the residual liquid substances are obtained. This liquid is subjected to gas chromatographic analysis (stationary phase: Silicone SE 30; column, 3 m; temperature-elevating rate, 5° C./min). The results are shown in Table 1.

For comparison, the reaction is effected in the same manner as above but not using chlorine. The results are also shown in Table 1.

| Example | Starting p-ClBTC or BTC | Temperature (°C.) | Cl₂/p-ClBTC or m-NO₂BTC or BTC (molar ratio) | HF/p-ClBTC or m-NO₂BTC or BTC (molar ratio) | Contact time (sec.) | Reaction products (mol %) | | | | Remarks |
|---|---|---|---|---|---|---|---|---|---|---|
| | | | | | | F₀ | F₁ | F₂ | F₃ | |
| 1 | p-ClBTC | 300 | 0.052 | 5.0 | 3.5 | 40 | 15 | 18 | 27 | |
| 2 | p-ClBTC | 298 | 0.075 | 5.2 | 3.6 | 11 | 24 | 25 | 40 | |
| 3 | p-ClBTC | 298 | 0.15 | 5.5 | 3.2 | 10 | 18 | 27 | 46 | |
| 4 | p-ClBTC | 400 | 0.052 | 5.9 | 2.8 | 0 | 4 | 26 | 70 | |
| 5 | p-ClBTC | 500 | 0.052 | 5.8 | 1.7 | 0 | 1 | 1 | 98 | |
| 6 | BTC | 400 | 0.052 | 5.8 | 2.7 | 0 | 1 | 2 | 97 | |
| 7 | m-NO₂BTC | 410 | 0.052 | 6.0 | 2.3 | 0 | 0 | 2 | 98 | |
| Comparative 1 | p-ClBTC | 301 | 0 | 4.9 | 3.6 | 43 | 34 | 20 | 3 | Tars observed in the reactor. |
| Comparative 1 | p-ClBTC | 400 | 0 | 5.6 | 1.8 | 21 | 22 | 43 | 14 | |

Note:

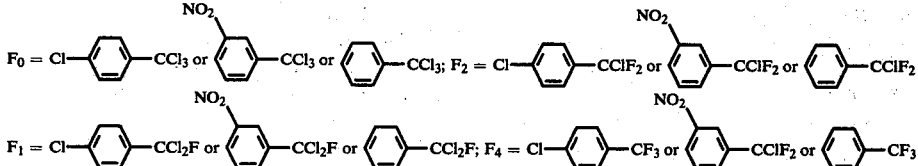

What is claimed is:

1. A process for preparing benzotrifluoride derivatives which comprises contacting a benzotrichloride compound of the formula:

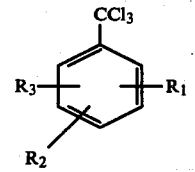

wherein $R_1$, $R_2$ and $R_3$ are each hydrogen, trichloromethyl, nitro, cyano or halogen but wherein all of $R_1$, $R_2$ and $R_3$ are not hydrogen at the same time and when one of $R_1$, $R_2$ and $R_3$ is nitro, each of the other two is not nitro, with hydrogen fluoride in the absence of any catalyst in the gaseous phase and in the presence of chlorine at an elevated temperature.

2. The process according to claim 1, wherein the hydrogen fluoride is used in a molar ratio of about 3 to 15 with respect to the benzotrichloride compound.

3. The process according to claim 1, wherein the chlorine is used in a molar ratio of not more than about 0.3 with respect to the benzotrichloride compound.

4. The process according to claim 1, wherein the contact is effected at a temperature of about 250° to 600° C.

5. The process according to claim 1, wherein the contact is effected for a period of at least about 0.2 second.

6. The process according to claim 1, wherein $R_1$, $R_2$ and $R_3$ are each hydrogen, trichloromethyl or halogen.

* * * * *